United States Patent [19]

Liebler

[11] Patent Number: 5,203,780
[45] Date of Patent: Apr. 20, 1993

[54] VENTED SURGICAL PROBE AND METHOD OF USE

[76] Inventor: William A. Liebler, 2 Village La., Bronxville, N.Y. 10708

[21] Appl. No.: 577,989

[22] Filed: Sep. 5, 1990

[51] Int. Cl.⁵ .............................................. A61B 17/36
[52] U.S. Cl. ...................... 606/14; 604/265; 606/15
[58] Field of Search .............. 604/21, 43–45, 604/35, 319; 606/4–7, 10–16, 40, 41, 49; 128/395–398

[56] References Cited

U.S. PATENT DOCUMENTS

| | | |
|---|---|---|
| 4,122,853 | 10/1978 | Smith . |
| 4,445,892 | 5/1984 | Hussein et al. . |
| 4,519,390 | 5/1985 | Horne . |
| 4,662,368 | 5/1987 | Hussein et al. . |
| 4,669,465 | 6/1987 | Moore et al. . |
| 4,744,360 | 5/1988 | Bath ............................ 606/16 |
| 4,747,405 | 5/1988 | Leckrone . |
| 4,790,310 | 12/1988 | Ginsburg . |
| 4,844,062 | 7/1989 | Wells . |
| 4,940,411 | 7/1990 | Vassiliadis et al. ............ 433/215 |
| 4,950,257 | 8/1990 | Hibbs et al. .................... 604/265 |
| 4,959,063 | 9/1990 | Kojima ............................ 606/15 |

FOREIGN PATENT DOCUMENTS 2826383 12/1979 Fed. Rep. of Germany .

Primary Examiner—Peter A. Aschenbrenner
Attorney, Agent, or Firm—Frishauf, Holtz, Goodman & Woodward

[57] ABSTRACT

An apparatus and method for venting off a surgical laser smoke plume which is generated when body tissue is treated by an optical fiber lasering device, comprising an elongated hollow needle through which an optical fiber laser member extends for emitting a laser beam at the tip of the needle which is adjacent to the body tissue to be treated. A vent side arm has one end which is attached to the needle, and another end which is connected to a suction device, so that when body tissue is treated by the laser beam emitted at the needle tip, the resulting smoke plume that is created will be suctioned up into the channel between the optical fiber strand and the inner surface of the needle and out the vent side arm into the suction device. An O-ring is attached at the outer end of the needle so that any surgical laser smoke plume that is being suctioned out does not escape into the atmosphere or back to the laser generator, but also goes out the vent side arm and into the suction device.

8 Claims, 2 Drawing Sheets

VENTED SURGICAL PROBE AND METHOD OF USE

BACKGROUND OF THE INVENTION

This invention relates generally to laser beam technology used in surgical procedures, and more specifically to an improved optical fiber laser device which allows for any hazardous surgical laser smoke plume, created as a result of lasering body tissue, to be safely evacuated from the patient's body and into a sealed suction device. In this way neither the treated body nor the surgical atmosphere are damaged or polluted by any viable microorganisms that may possibly be contained within the surgical laser smoke plume.

Studies published by Garden, J. et al, (1988) *Papillomavirus in the Vapor Carbon Dioxide Laser—Treated Verrucae,* JAMA 259:1199-1202 and also by Walker, N. et al (1986) *Possible Hazards from Irradiation with the Carbon Dioxide Laser,* LASERS IN SURGERY AND MEDICINE, 6:84-86 have shown that certain types of virulent DNA have been detected intact within the smoke plume that survive the vaporization of infected tissue by a laser.

A laser beam passing through a needle probe has been used as a tool for performing various surgical procedures, such as excising, cutting and denaturing various types of body tissues, and has also been used previously for various surgical procedures such as eye surgery (as in cataracts), removal of polyps of the vocal cords, growths in the intestinal tract, meniscectomies in the knee and arthroscopic debridement of various joints for synovitis.

No prior art, however, has provided a means to efficiently remove the potentially hazardous surgical laser smoke plume, which is produced as a result of cauterizing deep body tissue, from a treated body and the surrounding surgical atmosphere.

An object of the present invention is to provide a method and apparatus for safely and effectively removing surgical laser smoke plume from the treated body and surrounding surgical atmosphere, thereby keeping the patient, surgeons and their attending staff free from coming in contact with possibly hazardous viable cell tissues, viral DNA, carbonized tissue, surgical odors and sub-micron laser smoke debris.

SUMMARY OF THE INVENTION

The subject matter of this invention is to provide a device, or more specifically a surgical laser probe for receiving an Nd-YAG, KTP or other laser beam which is focused on a specific area of soft body tissue to be debulked or removed. The laser beam emitting from the probe vaporizes the body tissue that is being treated. This laser beam action on soft body tissue, such as cartilage in intervertebral discs and the meniscus of a knee, produces a surgical laser smoke plume and therefore, the present invention provides a method and apparatus for venting a surgical laser-type needle apparatus so that the smoke plume is properly evacuated.

The invention is particularly useful for performing laser surgery to decompress soft body tissue such as intervertebral discs in the vertebral spine.

An improved surgical needle probe for the administration of laser beam energy to treat a body part comprises an elongated hollow needle portion; an elongated optical fiber which passes through the hollow needle portion, wherein the needle is inserted at one end into a body tissue whereby an end of the optical fiber is placed adjacent to body tissue that is to be treated by the laser beam; a channel-like space provided between the elongated optical fiber and the inner surface of the hollow needle portion along at least a substantial portion of the length of the hollow needle portion and extending to the end of the hollow needle portion which is inserted into the body tissue; and evacuating means coupled to the needle and communicating with the channel-like space for evacuating any resulting hazardous smoke plume from the treated body portion and from the space.

According to a preferred feature of the invention, the evacuating means comprises a vent side arm coupled to a wall of the hollow needle portion and in communication with the channel-like space between the needle portion and the optical fiber; and a suction device coupled to the vent side arm; the vent side an being arranged between the hollow needle portion and the suction device, whereby a smoke plume resulting from the laser treatment is suctioned up the channel and into the vent side arm and then into the suction device. The suction device preferable also includes a filtering system for filtering the laser smoke plume.

Other objects, advantages and novel features of the invention will become apparent to those skilled in the art from the following detailed description of the invention when considered in conjunction with the accompanying drawings wherein the like reference numbers identify like parts throughout.

DETAILED DESCRIPTION OF THE INVENTION

Figure 1:
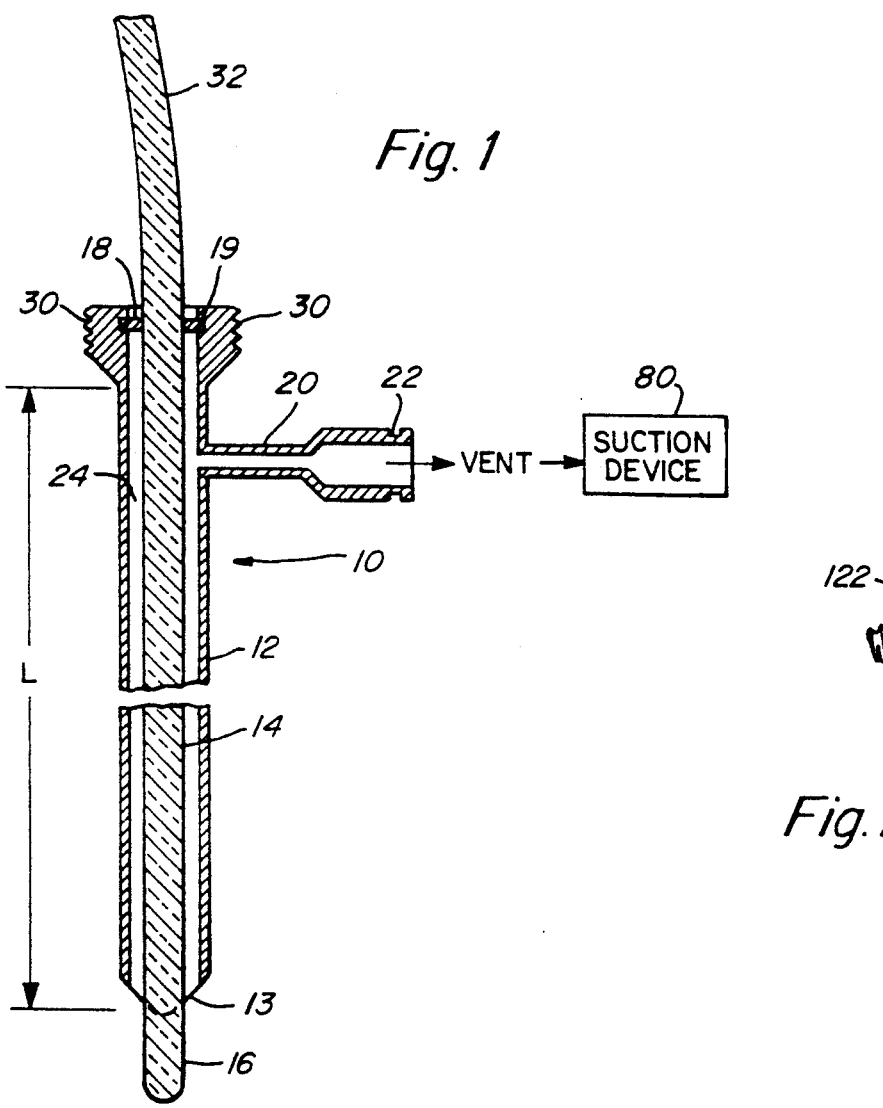
FIG. 1 is a sectional view of a probe of the present invention for use with a lasering system, and having a vent side arm and adapted to be attached to a suction device.

Referring to FIG. 1, a vented probe according to the present invention is shown in cross-section. The vented probe 10 comprises an outer tubular member 12, preferably made of a metallic material, such as stainless steel, which has a fiber optic laser light transmitting member 14 therein. The fiber optic member 14 extends out of the bottom or distal end portion of the tubular member 12 and has an exposed distal end portion 16, which transmits the laser energy to the body portion to be treated. The fiber optic member 14 passes completely through the tubular member 12 with a space (generally annular space) 24 therebetween. An O-ring sealing member 18 is provided at the upper portion of the device for providing an air-tight seal between the fiber optic member 14 and the inner wall of the tubular member 12. The O-ring 18 is seated in an annular groove 19 in the upper portion of tubular member 12. The advantage of the arrangement shown in FIG. 1 is that the airtight seal between the fiber optic member 14 and the inner surface of tubular member 12 prevents air or smoke or the like within space 24 from escaping to the outside, as will become apparent from the discussion hereinbelow. The O-ring 18 is preferably made of elastomeric material which is unaffected by the laser smoke plume, and is preferably slightly under compression to provide the desired air-tight seal. The compression is such as to permit sliding movement of the fiber optic member 14 relative to the tubular member 12 during use, while maintaining a substantially air-tight seal.

Figure 4:
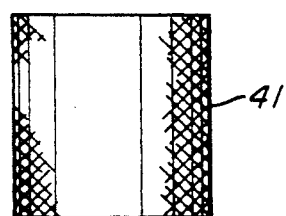
FIG. 4 shows a needle for use when inserting the device of the present invention into body tissue.

The outer upper surface of the tubular member 12 has a thread 30 thereon, which will be discussed below in conjunction with FIG. 4.

Figure 2:
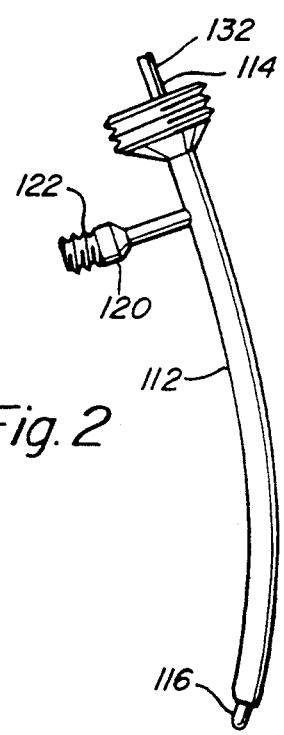
FIG. 2 shows a modified embodiment of the probe shown in FIG. 1.

The tubular member 12 has a side vent 20 which is shown in FIG. 1 as being integral with (for example by means of welding, brazing, soldering, or the like) tubular member 12. The vent member 20 has a fitting 22 at the end portion thereof for connection with a suction device 80 (shown schematically). The suction device 80 preferably includes a filtration system for filtering the laser smoke plume. The fitting 22 may be of the bayonet type (as shown in FIG. 1), a Leur lock, or it may be threaded (see FIG. 2) or any other suitable type of fitting. The inner hollow area of side vent member 20 is in communication with the space 24 between the outer wall of the fiber optic member 14 and the inner wall of the tubular member 12. FIG. 2 shows a curved embodiment, wherein reference numbers designating like parts as in FIG. 1 are incremented by 100. The curved member 112 is useful for some surgical procedures, as in some lower back procedures.

The upper end 32 of fiber optic member 14 is connected to a laser device, as is conventional. Also as is conventional, the fiber optic member 14 is coated with a cladding therearound for preventing leakage of laser energy therefrom, and for maintaining proper transmission of laser energy therethrough. The tip end portion 16 of fiber optic member 14 has the cladding removed, and is polished, for proper transmission of laser energy to the body part to be treated.

In use, the tubular member 12, with the exposed polished end 16 of the fiber optic member therein, is arranged in a body cavity and is placed adjacent the body portions to be treated. A typical insertion technique is described hereinbelow with reference to FIG. 4. Alternatively, the device can be inserted into a body cavity which has been opened in advance. Conventional image intensifier viewing devices are used in order to insure proper location and orientation of the distal end of tubular member 12 and the polished end 16 of the fiber optic laser energy transmitting member 14 adjacent the desired body part. Laser energy is supplied to the end portion 32 of the fiber optic member 14 in a conventional manner in order to treat the affected body part. The surgical laser smoke plume, generated as a result of the laser energy acting on the body part, is sucked upwardly through the space 24 by means of the suction developed by the suction device which is connected to the side vent arm 20. The sealing member, such as O-ring 18, prevents leakage of the surgical laser smoke plume out of the upper portion of the probe 10, and insures that all of the smoke plume is safely vented to the suction device which is connected to the side vent arm 20.

The venting channel 24 is critical to operation of the present invention. However, the size thereof is not critical, so long as sufficient space is provided to evacuate the surgical laser smoke plume by means of the suction developed by the conventional suction device.

In place of the O-ring 18, other sealing means could be used, such as rubber or other air-tight packing between the outer wall of the fiber optic member 14 and the inner wall of the tubular member 12.

The distal end 13 of the tubular member 12 is pointed and is preferably sharp so as to be able to pierce human body tissue. Often, in use, it is desired to use the outer tubular member 12 per se to pierce body tissue to locate the end portion thereof in the correct position within the body for treatment of internal body tissue. In order to carry this out, the fiber optic member 14 is removed by pulling same out of member 12, and an elongated needle member (40; FIG. 4) having a sharp end 42 is placed within the tubular member 12 so as to substantially fill the interior of the tubular member 12 and to serve as a lumen. The knurled knob 41 of the member 40 is screwed onto threaded portion 30 of the tubular member 12 to facilitate use. The needle 40 not only stiffens tubular member 12 and makes it easier to manipulate when piercing body tissue, but the elongated needle 40 fills or substantially fills the interior of the tubular member 12 and prevents body tissue from entering, thereby preventing body tissue from clogging the interior of the tubular member 12 during insertion into the body. After the device is inserted in the body, the knurled knob 41 is unscrewed from member 12 and the elongated needle member 40 is pulled out of the tubular member 12, and the fiber optic member 14 is inserted. The depth of insertion of fiber optic member 14, to provide the proper exposed laser energy emitting portion 16, is determined using a conventional image intensifier viewing device. Then, the system is ready for operation and treatment of body tissue, as described above. A typical needle 40 for insertion into the tubular member 12 is shown in FIG. 4. Other equivalents designs could be used. The needle 40 is preferably metal (stainless steel), or could be made of plastic material.

Figure 5:
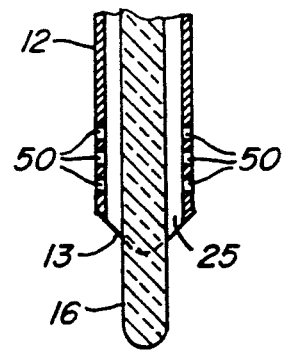
FIG. 5 shows a modified embodiment of the probe of FIG. 1.

FIG. 5 shows a fragmentary view of the lower portion of another embodiment of the probe of FIG. 1, wherein perforations are provided around the lower portion of the tubular member 12 to permit evacuation of the laser smoke plume, even if the lower end of space 24 becomes clogged or partially clogged with body tissue. The perforations 50 shown in FIG. 5 are preferably provided in addition to the lower opening 25 of space 24 at the distal end of the tubular member 12. The perforations 50 could be provided instead of the lower opening 25 of space 24, but this is not preferred.

Figure 6:
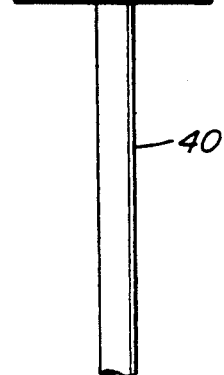
FIG. 6 shows the probe of FIG. 1 with a movement limiting device thereon.
Figure 6:
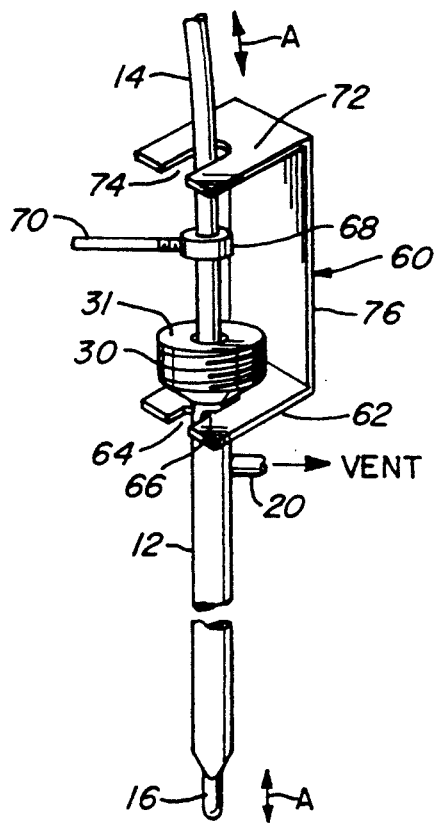

FIG. 6 shows a further modified embodiment comprising a generally U-shaped clip member 60 which clips and snaps over the upper end portion of tubular member 12, the purpose of which is to limit upward movement of the fiber optic member 14 during use. In use of the laser device of the present invention, it is often desirable to move the tip end 16 of the fiber optic device up and down in the direction of the arrows A in FIG. 6, during treatment of the body part. However, since the lower emission end 16 of the fiber optic member 14 emits high energy, it is necessary to prevent the emission end 16 from being moved upward within the metal tubular member 12, in order to prevent arcing of the laser beam to the metal tubular member 12. The clip 60 is provided to limit the upward travel of the fiber optic device 14 during use. The lower end 62 of the clip 60 has an opening 64 through which the upper portion of tubular member 12 is passed. Projections or bumps 66 are provided on the inner walls of opening 64 so as to snap over and lock onto the tubular member 12. An adjustable collar 68 is mounted around fiber optic member 14, and is locked in place by a threaded handle member 70 which threads into a threaded opening in a side wall of collar 68 so as bear on the fiber optic member 14 to lock the collar member in a predetermined position on the fiber optic member 14. The upper wall 72 of clip 60 has an opening 74 therein for receiving the fiber optic member 14.

In use, the position of the collar 68 is adjusted on the fiber optic member 14 so as to provide the appropriate predetermined upward and downward limited movement of the fiber optic member 14, to move the polished end 16 thereof up and down in the direction of arrows A between predetermined upper and lower limits. The lower limit position is determined by the upper surface 31 of tubular member 12 on which the collar 68 will bear when pushed downwardly, and the upper limit position is determined by the position of the upper surface 72 of clip 60, against which the collar 68 bears when it is moved to its uppermost position, to thereby limit upward movement of the fiber optic member 14.

The limits of movement can be adjusted in various ways. For example, the position and size of the collar 68 on fiber optic 14 will limit the movement, and the size and position of the clip 60 can also be varied to appropriately limit the movement. For example, clips 60 with different length back walls 76 can be provided, as desired. Alternatively, collars 68 having different vertical dimensions (or thicknesses in the vertical direction) could be used to provide differing limits of movement. The position of collar 68 on fiber optic 14 can be easily varied by loosening adjustment (and handle member) 70, reorienting the position of the collar member, and then tightening member 70 on the fiber optic member. Other suitable limit devices could be used, as desired. The degree of up and down movement shown in FIG. 6 is exaggerated for ease of explanation. Actually, shorter relative movements will be used.

The clip 60 shown in FIG. 6 can be used with the embodiment of FIG. 1, as well as with the embodiments of FIGS. 2 and/or 5.

In some cases, the probe of the present invention should be substantially straight, as shown in FIG. 1. However, in uses for treating body tissue such as spinal disks, located in the lower back of a patient, the tubular member 12 is preferably made curved, as shown by way of example in FIG. 2. The illustration in FIG. 2 is schematic only, and is being provided only to show the curved tubular member. As mentioned hereinabove, elements in FIG. 2 which correspond to those in FIG. 1 are given the same reference numerals, but incremented by 100. The internal construction, however, is the same. Since the fiber optic 40 is flexible, it conforms to the curvature of the tubular member 112, and an appropriate channel corresponding to channel 24 of FIG. 1 (not seen in FIG. 2) is formed between the outer surface of the fiber optic member 114 and the inner surface of the tubular member 112.

In a preferred embodiment, the tubular member 12 is fabricated from a 15 gauge hollow needle (stainless steel preferably); the length "L" of the tubular member 12 of FIG. 1 (and of member 112 of FIG. 2) is approximately 8 inches; and the polished portion 16 of the fiber optic member 14 projects about 1 cm from the end of the tubular member 12. However, the cladding is maintained around the projecting portion 16 at least at the portion where it is adjacent the end of tubular member 12, to prevent arcing or the like. Only the polished tip end portion 16 which is clearly outside of the tubular member 12 is exposed to deliver laser energy to a body portion. The fiber optic member is preferably about 0.5 mm (600 microns) in diameter, and tightly fits within the opening of O-ring 18 to provide an appropriate air-tight seal. An 18 gauge needle 12 could also be used, but the space 24 would be smaller.

The suction device 80 shown schematically in FIG. 1 can be any of various well known types of suction devices or smoke evacuators which are used with lasers during surgery. Such conventional suction devices are generally used with additional separate suction tubes which are placed in the surgical area to evacuate smoke during surgery. This is disadvantageous, since separate tubes are required, additional space is needed, the views may be blocked, the surgical opening must be larger, etc. In the present invention, such conventional suction devices would instead be connected to the vent side arm 20 (120). One such known laser smoke suction and filtration system is manufactured by Stack House, Inc., Manhattan Beach, California (Model Point One System; and Model LFA-100 Laser Smoke Filtration System). The inputs to these known suction and filtration systems are modified so as to be connected to the vent side arm 20 (120) of the present invention instead of to a separate tube or the like.

Figure 3:
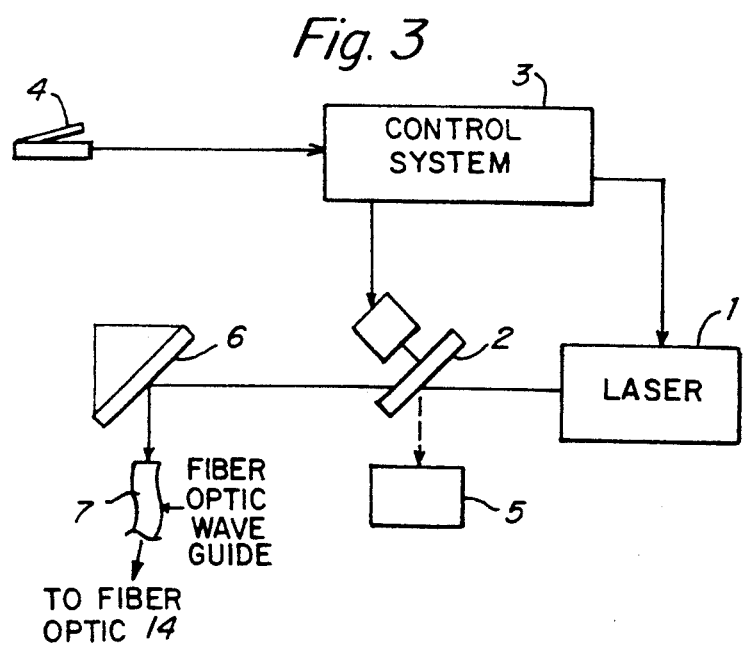
FIG. 3 schematically illustrates an overall lasering system in which the present invention is usable.

In FIG. 3, there is shown one embodiment of a complete lasering system which is comprised of a laser beam generator 1 for delivering a collimated laser beam, and a shutter 2 which is controlled by control system 3 operated by a foot pedal switch 4. The control system 3 is set by an operator to control the intensity and duration of the laser beam energy to be applied on the area being treated. The shutter 2 normally blocks the laser beam from the generator 1 and diverts it to a power meter 5, prior to exposure for treatment. When the shutter 2 is open, the beam is deflected by a mirror 6 into the near end of an optical fiber wave guide 7 which is coupled to the fiber optic member 14 of FIG. 1. The mirror 6 provides alignment of the laser beam with the access portion of the first segment of the optical fiber wave guide 7. The laser beam is delivered through the flexible optical fiber 7, 14 for treatment of a localized body area. Once the localized area of the body tissue is treated, any hazardous smoke plume, created as a result of said laser treatment will be drawn up the passageway or channel 24 (FIG. 1) by suction from the suction device, into the vent side arm 20, and then safely evacuated into a sealed suction device. In this way neither the treated body nor the surgical atmosphere are damaged or polluted by any viable microorganisms contained within the surgical laser smoke plume.

The laser system of FIG. 3 is only exemplary. Other known laser systems could be used, such as that shown in the publication "Endoscopic Laser Surgery Handbook", Stanley Shapshay, Marcel Dekker, Inc., 1987, section entitled "Physics and Interaction with Soft Tissue, page 49, FIG. 12 the contents of which are incorporated herein by reference.

In the particular embodiment described herein, treatment of a spinal disc is referred to, but the disclosed device can be used for treatment of any body tissue that produces a smoke plume as a result of being subjected to lasering.

I claim:

1. A surgical needle probe for the administration of laser beam energy to treat a body part, comprising:

an elongated hollow needle portion having an inner surface;

an elongated optical fiber which passes through said hollow needle portion, said optical fiber having an outer surface, and said optical fiber being movable relative to said hollow needle portion in the longitudinal direction of said hollow need portion, and wherein said hollow needle portion has one end which is insertable into a body tissue whereby an end of said optical fiber is placed adjacent to a body portion that is to be treated by a laser beam passing through said optical fiber;

said optical fiber having a distal end portion at which said laser beam is emitted, said distal end portion of said optical fiber extending beyond said one end of said hollow needle portion during treatment of the body portion so as to be directly adjacent the body portion to be treated;

a channel-like space provided between said outer surface of said elongated optical fiber and said inner surface of said hollow needle portion and extending along at least a substantial portion of the length of said hollow needle portion, and said channel-like space substantially surrounding said optical fiber within said hollow needle portion and extending to said one end of said hollow needle portion which is insertable into the body tissue, thereby providing a ring-like opening at said one end of said hollow needle portion;

evacuating means coupled to said hollow needle portion at a location remote from said one end of said hollow needle portion, and said evacuating means communicating with said channel-like space for evacuating any resulting hazardous smoke plume, produced by treating said body portion with said laser beam, from said channel-like space via said ring-like opening;

a vent side arm coupled to a wall of said hollow needle portion and in communication with said channel-like space between said hollow needle portion and said optical fiber;

said evacuating means including a suction device coupled to said vent side arm;

said vent side arm being connected between said hollow needle portion and said suction device, whereby a smoke plume resulting from the laser treatment is suctioned up said channel-like space and into said vent side arm and then into said suction device;

sealing means in said channel-like space between said outer surface of said elongated optical fiber and said inner surface of said hollow needle portion for providing a substantially air-tight seal therebetween, said sealing means being located above said vent side arm relative to said one end of said hollow needle portion; and movement limiting means coupled to said hollow needle portion and to said optical fiber for limiting relative movement therebetween;

said movement limiting means comprising an abutment member on said optical fiber, and a generally U-shaped clip member coupled to said hollow needle portion, said U-shaped clip member having at least one movement limiting surface thereon which is abuttable by said abutment member on said optical fiber to limit movement of said optical fiber, relative to said hollow needle portion.

2. The surgical needle probe of claim 1, wherein said vent side arm is located between said sealing means and said one end of said hollow needle portion, and is arranged closer to said sealing means.

3. The surgical needle probe of claim 1, wherein said sealing means comprises an elastomeric member arranged between said optical fiber and said inner surface of said hollow needle portion.

4. The surgical needle probe of claim of 3, wherein said elastomeric member is in compression to provide a substantially air-tight seal, and permits relative movement between said optical fiber and said hollow needle portion in the longitudinal direction of said hollow needle portion.

5. The surgical needle probe of claim 1, wherein said abutment member is adjustably mounted on said optical fiber so as to vary its position along said optical fiber.

6. The surgical needle probe of claim 1, further comprising an elongated needle member removably insertable within said hollow needle portion when said optical fiber is not inserted therein, for use in piercing a body part, said elongated needle member being removable from said hollow needle portion thereafter, and said elongated optical fiber being insertable in said hollow needle portion after said elongated needle is removed therefrom.

7. The surgical needle probe of claim 1, further comprising at least one perforation at a distal portion of said elongated hollow needle portion adjacent the distal end thereof.

8. A surgical needle probe for the administration of laser beam energy to treat a body part, comprising:

an elongated hollow needle portion having an inner surface;

an elongated optical fiber which passes through said hollow needle portion, said optical fiber having an outer surface, and said optical fiber being movable relative to said hollow needle portion in the longitudinal direction of said hollow need portion, and wherein said hollow needle portion has one end which is insertable into a body tissue whereby an end of said optical fiber is placed adjacent to a body portion that is to be treated by a laser beam passing through said optical fiber;

said optical fiber having a distal end portion at which said laser beam is emitted, said distal end portion of said optical fiber extending beyond said one end of said hollow needle portion during treatment of the body portion so as to be directly adjacent the body portion to be treated;

a channel-like space provided between said outer surface of said elongated optical fiber and said inner surface of said hollow needle portion and extending along at least a substantial portion of the length of said hollow needle portion, and said channel-like space substantially surrounding said optical fiber within said hollow needle portion and extending to said one end of said hollow needle portion which is insertable into the body tissue, thereby providing a ring-like opening at said one end of said hollow needle portion;

evacuating means coupled to said hollow needle portion at a location remote from said one end of said hollow needle portion, and said evacuating means communicating with said channel-like space for evacuating any resulting hazardous smoke plume, produced by treating said body portion with said laser beam, from said channel-like space via said ring-like opening;

a vent side arm coupled to a wall of said hollow needle portion and in communication with said channel-like space between said hollow needle portion and said optical fiber;

said evacuating means including a suction device coupled to said vent side arm;

said vent side arm being connected between said hollow needle portion and said suction device, whereby a smoke plume resulting from the laser treatment is suctioned up said channel-like space and into said vent side arm and then into said suction device;

sealing means in said channel-like space between said outer surface of said elongated optical fiber and said inner surface of said hollow needle portion for providing a substantially air-tight seal therebetween, said sealing means being located above said vent side arm relative to said one end of said hollow needle portion; and movement limiting means coupled to said hollow needle portion and to said optical fiber for limiting relative movement therebetween;

said movement limiting means comprising an abutment member on said optical fiber, and a movement limiting member coupled to said hollow needle portion, said movement limiting member having at least one movement limiting surface thereon which is abuttable by said abutment member on said optical fiber to limit movement of said optical fiber, relative to said hollow needle portion, and wherein said abutment member is adjustably mounted on said optical fiber so as to vary its position along said optical fiber.

* * * * *